United States Patent [19]

Baumann et al.

[11] 4,110,348
[45] Aug. 29, 1978

[54] 7,7'-DIAMINO DERIVATIVES OF 2,2'-SPIRODIBENZOPYRANES

[75] Inventors: Hans Baumann, Wachenheim; Andreas Oberlinner, Ludwigshafen, both of Fed. Rep. of Germany

[73] Assignee: BASF Aktiengesellschaft, Ludwigshafen, Fed. Rep. of Germany

[21] Appl. No.: 773,337

[22] Filed: Mar. 1, 1977

[30] Foreign Application Priority Data

Mar. 19, 1976 [DE] Fed. Rep. of Germany ....... 2611600

[51] Int. Cl.$^2$ .......................................... C07D 311/02
[52] U.S. Cl. ........................ 260/345.2; 544/62; 544/150; 260/268 H; 260/293.53; 260/293.58; 260/326.11 S; 260/326.8; 260/326.85; 8/7; 544/70; 544/230; 544/79; 542/454
[58] Field of Search ....................................... 260/345.2

[56] References Cited

U.S. PATENT DOCUMENTS

| | | | |
|---|---|---|---|
| 2,978,462 | 4/1961 | Berman et al. | 260/345.2 |
| 3,666,525 | 5/1972 | Kimura et al. | 260/345.2 |
| 3,810,762 | 5/1974 | Laridon et al. | 260/345.2 |
| 3,810,763 | 5/1974 | Laridon et al. | 260/345.2 |
| 3,899,514 | 8/1975 | Baumann et al. | 260/345.2 |
| 3,971,808 | 7/1976 | Baumann et al. | 260/345.2 |

*Primary Examiner*—Nicky Chan
*Attorney, Agent, or Firm*—Keil, Thompson & Shurtleff

[57] ABSTRACT

Dye intermediates of the formula

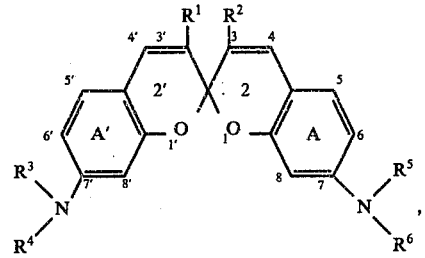

where $R^1$ is hydrogen, alkyl of 1 to 12 carbon atoms, phenyl which is unsubstituted or substituted by alkyl of 1 to 4 carbon atoms, methoxy, ethoxy, chlorine or bromine, or phenylalkyl of 7 to 10 carbon atoms, $R^2$ is hydrogen or $R^1$ and $R^2$ together are dimethylene, trimethylene or tetramethylene, which are unsubstituted or substituted by alkyl of 1 to 12 carbon atoms, $R^3$ and $R^5$ are hydrogen, alkyl of 1 to 12 carbon atoms, cyano-, chlorine-, methoxy- or ethoxy-substituted alkyl of 2 to 4 carbon atoms, cycloalkyl of 5 to 7 carbon atoms, phenylalkyl of 7 to 10 carbon atoms or trimethylene which is unsubstituted or substituted by 1 to 3 methyl and is bonded to the carbon atom in the 6-position or 6'-position of the benzene ring, $R^4$ and $R^6$ are alkyl of 1 to 12 carbon atoms, cyano-, chlorine-, methoxy- or ethoxy-substituted alkyl of 2 to 4 carbon atoms, phenylalkyl of 7 to 10 carbon atoms, phenyl which is unsubstituted or substituted by alkyl of 1 to 4 carbon atoms, chlorine or bromine, or trimethylene bonded to the carbon atom in the 8-position or 8'-position of the benzene ring, or one or both of the groups

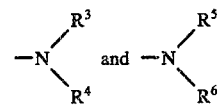

are a pyrrolidine, piperidine, morpholine, thiomorpholine, N'-alkylpiperazine (alkyl being of 1 to 4 carbon atoms) or iso-indoline radical, and the substituents $R^3$, $R^4$, $R^5$ and $R^6$ may be identical or different and the rings A and A' may be substituted by alkyl of 1 to 3 carbon atoms.

The dye intermediates give deep bluish-green to green colorations with electron-attracting substances and may be used for the manufacture of pressure-sensitive recording materials.

8 Claims, No Drawings

7,7'-DIAMINO DERIVATIVES OF 2,2'-SPIRODIBENZOPYRANES

The present invention relates to dye intermediates of the general formula I

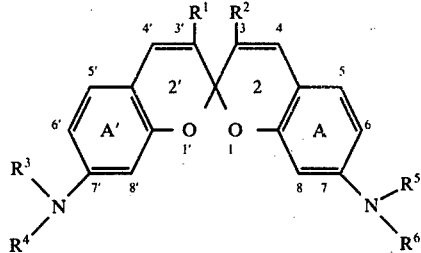

where $R^1$ is hydrogen, alkyl of 1 to 12 carbon atoms, phenyl which is unsubstituted or substituted by alkyl of 1 to 4 carbon atoms, methoxy, ethoxy, chlorine or bromine, or phenylalkyl of 7 to 10 carbon atoms, $R^2$ is hydrogen or $R^1$ and $R^2$ together are dimethylene, trimethylene or tetramethylene, which are unsubstituted or substituted by alkyl of 1 to 12 carbon atoms, $R^3$ and $R^5$ each are hydrogen, alkyl of 1 to 12 carbon atoms, cyano-, chlorine-, methoxy- or ethoxy-substituted alkyl of 2 to 4 carbon atoms, cycloalkyl of 5 to 7 carbon atoms, phenylalkyl of 7 to 10 carbon atoms or trimethylene which is unsubstituted or substituted by 1 to 3 methyl and is bonded to the carbon atom in the 6-position or 6'-position of the benzene ring, $R^4$ and $R^6$ each are alkyl of 1 to 12 carbon atoms, cyano-, chlorine-, methoxy- or ethoxy-substituted alkyl of 2 to 4 carbon atoms, phenylalkyl of 7 to 10 carbon atoms, phenyl which is unsubstituted or substituted by alkyl of 1 to 4 carbon atoms, chlorine or bromine, or trimethylene bonded to the carbon atom in the 8-position or 8'-position of the benzene ring, or one or both of the groups

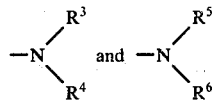

are a pyrrolidine, piperidine, morpholine, thiomorpholine, N'-alkylpiperazine (alkyl being of 1 to 4 carbon atoms) or isoindoline radical, and the substituents $R^3$, $R^4$, $R^5$ and $R^6$ may be identical or different and the rings A and A' are unsubstituted or substituted by alkyl of 1 to 3 carbon atoms.

Examples of substituents $R^1$ are, apart from hydrogen, alkyl of 1 to 12 carbon atoms, eg. methyl, ethyl, propyl, β-methylpropyl, n-butyl, hexyl, octyl, nonyl, decyl and dodecyl, unsubstituted or substituted phenyl, eg. phenyl, p-tolyl, p-ethylphenyl, p-propylphenyl, p-tert.-butylphenyl, p-methoxyphenyl, β-ethoxyphenyl, chlorophenyl and bromophenyl, and phenylalkyl of 7 to 10 carbon atoms, eg. benzyl, β-phenylethyl, β-phenylpropyl, γ-phenylpropyl and δ-phenylbutyl.

Specific examples of $R^1$ and $R^2$ as dimethylene, trimethylene or tetramethylene which may be unsubstituted or substituted by alkyl of 1 to 12 carbon atoms are dimethylene, trimethylene, β-alkyltrimethylene (where alkyl is of 1 to 12 carbon atoms), eg. β-methyltrimethylene, β-tert.-butyltrimethylene, β-n-heptyltrimethylene, β-n-octyltrimethylene, β-n-nonyl-trimethylene, β-n-dodecyltrimethylene and tetramethylene.

For tinctorial and technological reasons, dye intermediates of the formula I, where $R^1$ is phenyl or $R^1$ and $R^2$ are trimethylene which in the β-position carries an alkyl radical of 1 to 12 carbon atoms, preferably alkyl of 4 to 12 carbon atoms, eg. tert.-butyl, heptyl, octyl, nonyl or dodecyl, are preferred.

Specific examples of radicals $R^3$, $R^4$, $R^5$ and $R^6$ are, amongst alkyl which may or may not be substituted, methyl, ethyl, propyl, butyl, hexyl, octyl, decyl, dodecyl, β-chloroethyl, β-cyanoethyl, β-methoxyethyl, γ-methoxypropyl, γ-ethoxypropyl and β-ethoxyethyl and, amongst phenylalkyl of 7 to 10 carbon atoms, benzyl, β-phenylethyl, γ-phenylpropyl, β-phenylpropyl and δ-phenylbutyl. Of these, the preferred meanings of $R^3$, $R^4$, $R^5$ and $R^6$ are alkyl of 1 to 6 carbon atoms and benzyl; $R^3$ and $R^5$ may, in addition, be cycloalkyl of 5 to 7 carbon atoms, especially cyclohexyl.

$R^4$ and $R^6$ may also be phenyl which may or may not be substituted, eg. phenyl, tolyl, chlorophenyl, bromophenyl, ethylphenyl or butylphenyl.

For tinctorial and technological reasons, methyl, ethyl, butyl, propyl, hexyl and/or benzyl are particularly preferred amongst the radicals mentioned for $R^3$, $R^4$, $R^5$ and $R^6$.

Very particularly preferred dye intermediates (I) are those where

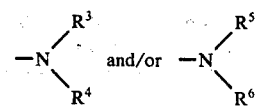

are dimethylamino, diethylamino, dipropylamino, dibutylamino, dihexylamino or dibenzylamino and where

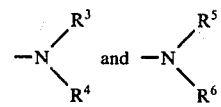

are identical or different.

The spirodipyrans of the formula I are pale-colored to colorless compounds. Their solutions in an inert, organic solvent give bluish-green to green colorations in contact with electron-attracting substances. Typical examples of electron acceptors are carboxylic acids and mineral acids, kaolin, bentonite, activated clay, aluminum silicate, attapulgite or any desired clay, acidic polymeric materials, eg. condensation products of phenols and/or phenolsulfonic acids, and metal oxides or salts, eg. zinc oxide, aluminum oxide, zinc chloride, iron stearate or cobalt naphthenate.

Because of these properties, the new compounds of the formula I can be used as chromogens (dye intermediates) in pressure-sensitive recording materials, copying materials or other pressure-sensitive duplicating systems.

Preferably, the compounds according to the invention, in organic solvents such as chlorinated paraffins, halogenated or partially hydrogenated biphenyl, alkylbenzenes, alkylnaphthalenes, alkylated dibenzylbenzene, paraffin oil, mineral oil or conventional solvents such as toluene or xylene, are enclosed, in the form of a solution or suspension, in micro-capsules and are used in this form for the manufacture of papers for pressure-sensitive copying processes. On contact with electron-attracting materials under appropriate pressure due to writing or typewriting, a bluish-green to green coloration is produced.

For this purpose, spirodipyrans of the formulae

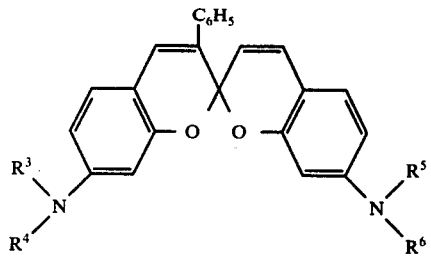 (Ia) and

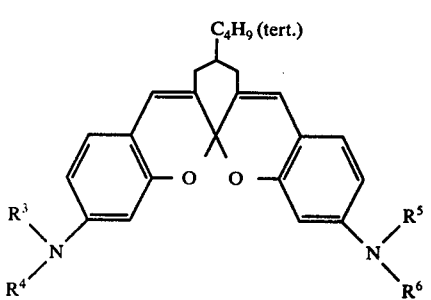 (Ib), where $R^3$, $R^4$, $R^5$ and $R^6$ are methyl, ethyl, butyl, propyl, hexyl and/or benzyl, are preferred for technological reasons. The compounds of the formulae

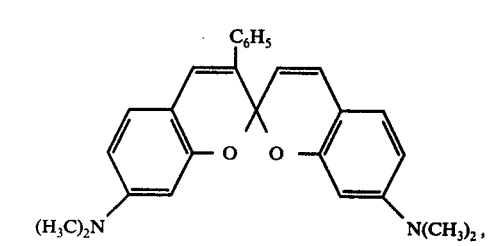

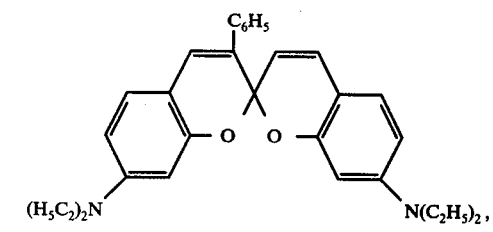

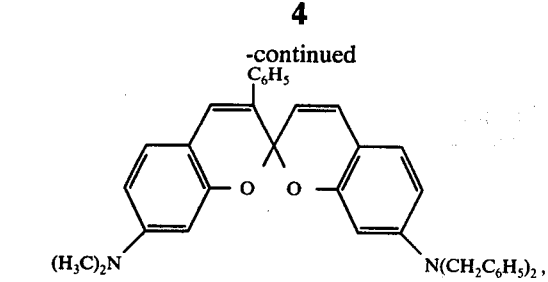

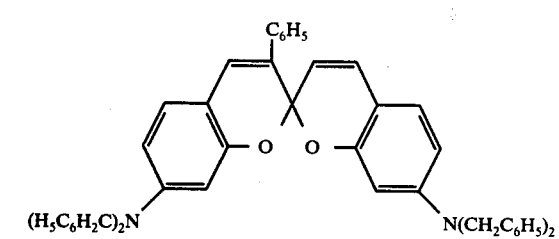

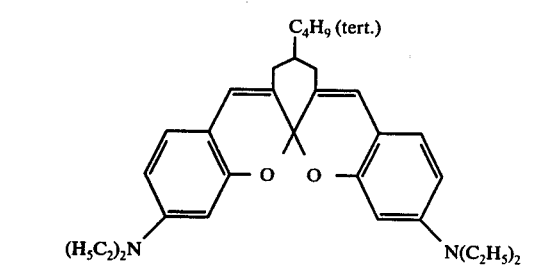

and

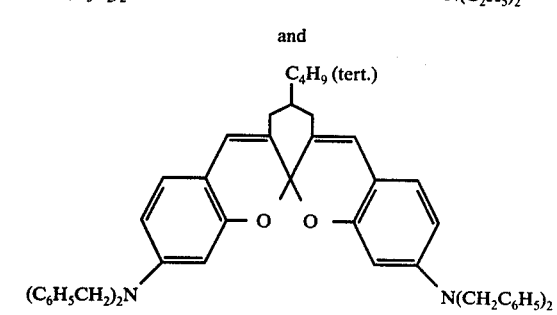

are very particularly preferred for tinctorial and technological reasons.

The dye intermediates I are synthesized by cyclizing the o-hydroxyaryl-styryl compounds of the formula IV. The compounds of the formula IV can be obtained, for example, by condensing benzopyrylium salts of the formula II with N-substituted p-aminosalicylaldehydes of the formula III. The compounds of the formula IV can also be manufactured by condensing the ketones of the formula V with the aldehydes of the formula III or by reacting the chalcones of the formula VI with the aldehydes of the formula III by conventional methods in accordance with the following equations:

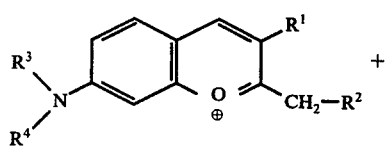

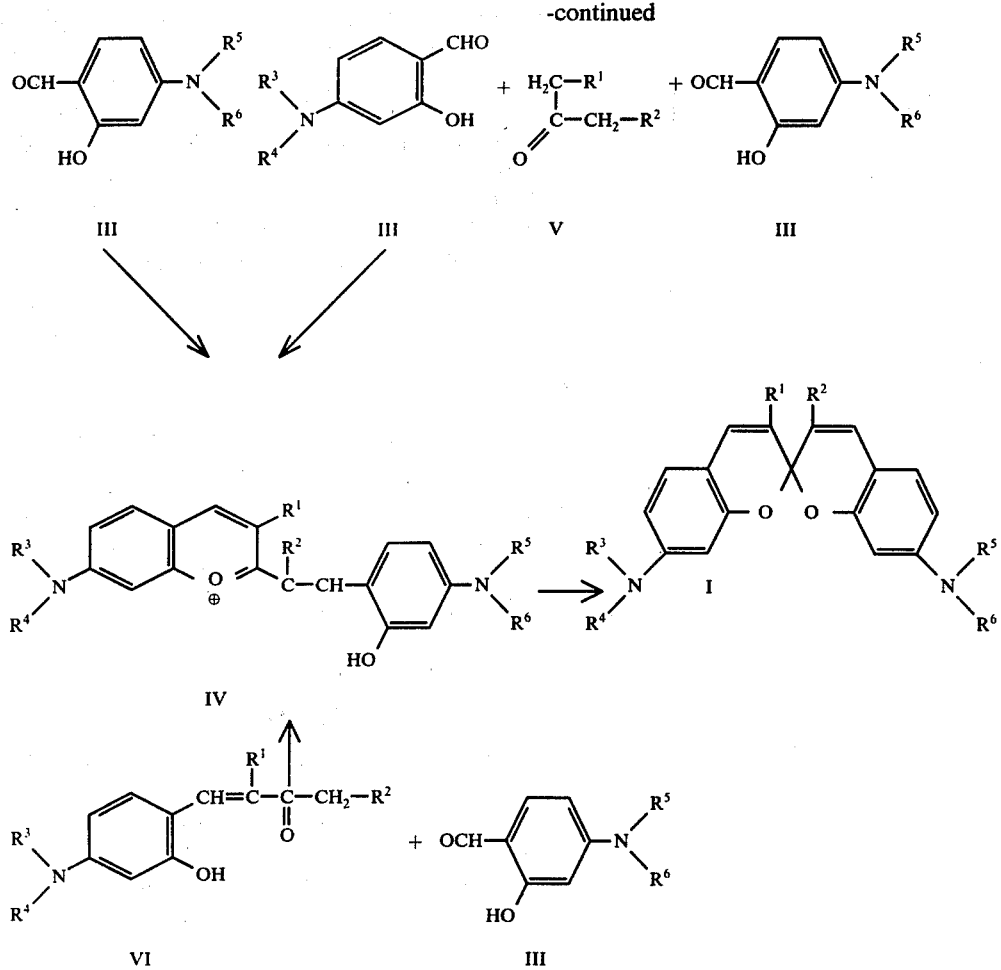

The condensations are advantageously carried out in organic solvents which are liquid at the reaction temperature, eg. alcohols, carboxylic acids, carboxylic acid anhydrides, carboxylic acid amides, hydrocarbons or acetonitrile, in the presence or absence of acid or basic condensing agents, eg. zinc chloride, phosphoric acid, hydrogen chloride, toluenesulfonic acid, boric acid, pyridine, piperidine, triethylamine or ammonium acetate in the conventional amounts for condensation reactions of the type in question.

As a rule, the condensation is carried out at from 20° to 120° C.

The cyclization of (IV) to give the pyran derivative can be carried out together with the condensation or following the latter, in the same or a separate process stage, by conventional methods, in the presence or absence of basic agents, eg. sodium hydroxide, potassium hydroxide, sodium carbonate, potassium carbonate, sodium acetate, potassium acetate, ammonia, aliphatic amines or pyridine. The crystalline spirodipyran compounds which separate out from this solution can be used, directly or after purification, eg. by recrystallization or reprecipitation, as dye intermediates for copying processes.

Examples of suitable starting compounds of the formulae II, III and V, for the manufacture of the compounds (IV), are:

a. Benzopyrylium salts of the formula II in the form of their chlorides, perchlorates, tetrafluoborates, tetrachloroferrates and trichlorozincates, in particular 2-methyl-3-phenyl-7-dimethylamino-benzopyrylium, 2-methyl-3-phenyl-7-diethylamino-benzopyrylium, 2-methyl-3-phenyl-7-dibenzylamino-benzopyrylium, 2-methyl-3-p-tolyl-7-dimethylamino-benzopyrylium, 2-methyl-3-p-anisyl-7-diethylamino-benzopyrylium, 2-methyl-3-p-chlorophenyl-7-diethylamino-benzopyrylium, 2-methyl-7-diethylamino-benzopyrylium and 2-methyl-7-dimethylamino-benzopyrylium salts.

b. Suitable aldehydes of the formula III are all above the compounds of the formula XI a (with Z=H) mentioned in German Laid Open Application DOS 2,413,281. Specific examples are: 4-dimethylaminosalicylaldehyde, 4-dimethylamino-5-methyl-salicylaldehyde 4-$\beta$-cyanoethyl-methylaminosalicylaldehyde, 4-di-$\beta$-cyanoethylaminosalicylaldehyde, 4-di-n-propylamino-salicylaldehyde, 4-di-n-butylaminosalicylaldehyde, 4-di-n-hexylaminosalicylaldehyde, 4-di-n-dodecylaminosalicylaldehyde, 4-cyclohexylamino-salicylaldehyde, 4-$\beta$-methoxyethyl-methylamino-salicylaldehyde, 4-di-$\beta$-chloroethylamino-salicylaldehyde, 4-dibenzylamino-salicylaldehyde, 4-N-pyrrolidyl-salicylaldehyde, 4-N-piperidinyl-salicylaldehyde, 4-(N'-methyl-N-piperazinyl)-salicylaldehyde, 4-N-morpholinyl-salicylaldehyde and 4-N-isoindolinyl-salicylaldehyde, as well as the o-hydroxy-benzaldehydes of the formulae

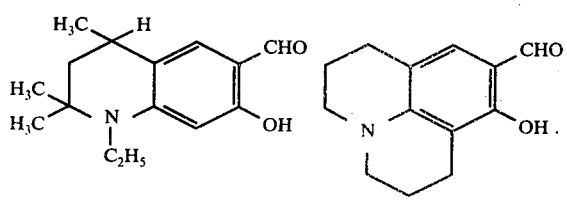

c. Specific examples of suitable ketones of the formula V are acetone, methyl ethyl ketone, methyl isobutyl ketone, 5-methylhexan-2-one, tridecan-2-one, phenylacetone, p-tolylacetone, p-anisylacetone, p-chlorophenylacetone, p-ethoxyphenylacetone, p-bromophenylacetone, benzylacetone, 1-phenyl-pentan-4-one, 1-phenylhexan-5-one, cyclohexanone, 4-tert.-butyl-cyclohexanone, 4-n-octylcyclohexanone, 4-n-heptyl-cyclohexanone, 4-n-nonyl-cyclohexanone, 4-n-dodecyl-cyclohexanone, cyclopentanone and cycloheptanone.

d. Examples of compounds of the formula VI are:
1-(o-hydroxy-p-dimethylamino-phenyl)-2-phenyl-but-1-en-3-one,
1-(o-hydroxy-p-diethylamino-phenyl)-2-phenyl-but-1-en-3-one,
1-(o-hydroxy-p-dimethylamino-phenyl)-2-(p-tolyl)-but-1-en-3-one,
1-(o-hydroxy-p-dibenzylamino-phenyl)-2-phenyl-but-1-en-3-one,
1-(o-hydroxy-p-pyrrolidino-phenyl)-2-phenyl-but-1-en-3-one and
1-(o-hydroxy-p-diethylamino-phenyl)-2-(p-anisyl)-but-1-en-3-one.

The preparation and isolation of the new compounds of the formula I is explained in more detail in the Examples which follow. In these, parts are by weight.

EXAMPLE 1

24.5 parts of 2-methyl-3-phenyl-7-diethylaminobenzopyrylium tetrachloroferrate and 9.6 parts of p-diethylaminosalicylaldehyde in 100 parts of alcohol are heated under reflux for 1 hour. Hydrogen chloride gas is then passed into the reaction solution at from 40° to 50° C until saturation is reached, after which the mixture is stirred for 3 hours at 20° C. The crystalline dye is isolated and stirred in 30 parts of 25 percent strength ammonia solution and 100 parts of toluene until completely decolorized. The toluene phase is separated off and concentrated to one-fifth. 11.5 parts of 3'-phenyl-7,7'-bis-diethylamino-2,2'-spirodi-(2H-1-benzopyran) of the formula

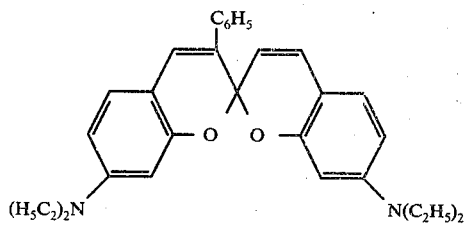

are precipitated from this solution by adding 50 parts of alcohol.

Melting point 170° - 172° C.

If a solution of this compound is enclosed in microcapsules and coated onto paper and the coated side is laid on an acid receptive coating, a green coloration is produced on the latter when writing on the paper so as to destroy the capsules and bring their contents into contact with the receptive coating.

EXAMPLE 2

Condensing 2-methyl-3-phenyl-7-diethylamino-benzopyrylium tetrachloroferrate with p-dimethylaminosalicylaldehyde by the method described in Example 1 gives 3'-phenyl-7-dimethylamino-7'-diethylamino-2,2'-spirodi-(2H-1-benzopyran) of the formula

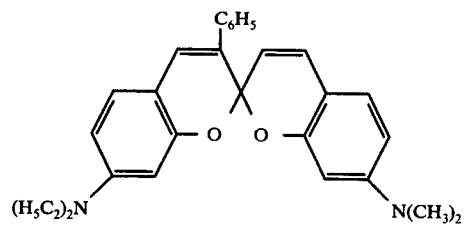

having a melting point of 212° - 214° C.

In contact with acidic substances, this compound gives a green coloration.

EXAMPLE 3

Reacting 2-methyl-3-phenyl-7-dimethyl-aminobenzopyrylium tetrachloroferrate with p-dimethylaminosalicylaldehyde by the method described in Example 1 gives 3'-phenyl-7,7'-bis-dimethylamino-2,2'-spirodi-(2H-1-benzopyran) of the formula

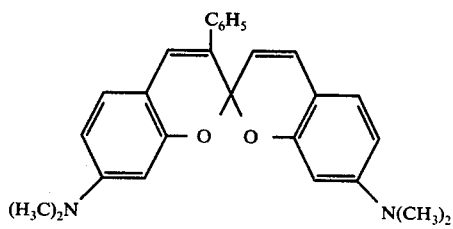

having a melting point of 217° - 218° C.

In contact with acidic substances, the compound develops a green coloration.

EXAMPLE 4

Condensing 2-methyl-3-phenyl-7-dimethylaminobenzopyrylium tetrachloroferrate by the method described in Example 1 with p-diethylaminosalicylaldehyde gives 3'-phenyl-7-diethylamino-7'-dimethylamino-2,2'-spirodi-(2H-1-benzopyran) of the formula

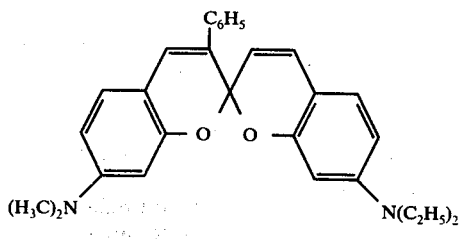

The compound melts at 143° - 144° C and gives a green coloration in contact with acidic substances.

EXAMPLE 5

| Ex. | R¹ | R² | R³ | R⁴ | R⁵ | R⁶ | Hue |
|---|---|---|---|---|---|---|---|
| 7 | p-H₃CC₆H₄— | H | CH₃ | CH₃ | CH₃ | CH₃ | green |
| 8 | p-H₃COC₆H₄— | H | C₂H₅ | C₂H₅ | C₂H₅ | C₂H₅ | green |
| 9 | p-ClC₆H₄— | H | C₂H₅ | C₂H₅ | C₂H₅ | C₂H₅ | green |
| 10 | —C₆H₅ | H | C₂H₅ | C₂H₅ | CH₃ | p-ClC₆H₄ | green |
| 11 | —C₆H₅ | H | C₂H₅ | C₂H₅ | CH₃ | p-H₃CC₆H₄ | green |
| 12 | —H | H | C₂H₅ | C₂H₅ | C₂H₅ | C₂H₅ | bluish green |
| 13 | —C₆H₅ | H | C₂H₅ | C₂H₅ | —(CH₂)₅— | | green |
| 14 | —C₆H₅ | H | C₂H₅ | C₂H₅ | —(CH₂)₄— | | green |
| 15 | —C₆H₅ | H | C₂H₅ | C₂H₅ | —(CH₂)₂O(CH₂)₂— | | green |
| 16 | —C₆H₅ | H | CH₃ | CH₃ | C₆H₁₃(n) | C₆H₁₃(n) | green |
| 17 | —C₆H₅ | H | CH₃ | CH₃ | C₃H₇(n) | C₃H₇(n) | green |
| 18 | C₆H₅ | H | CH₃ | CH₃ | C₄H₉(n) | C₄H₉(n) | green |
| 19 | C₆H₅ | H | CH₃ | CH₃ | C₁₂H₂₅(n) | C₁₂H₂₅(n) | green |
| 20 | CH₂C₆H₅ | H | CH₃ | CH₃ | CH₃ | CH₃ | bluish green |
| 21 | C₂H₄C₆H₅ | H | CH₃ | CH₃ | CH₃ | CH₃ | bluish green |
| 22 | CH₃ | H | CH₃ | CH₃ | CH₃ | CH₃ | bluish green |
| 23 | CH₂CH(CH₃)₂ | H | CH₃ | CH₃ | CH₃ | CH₃ | bluish green |
| 24 | C₁₀H₂₁(n) | H | CH₃ | CH₃ | CH₃ | CH₃ | bluish green |
| 25 | C₃H₆C₆H₅ | H | CH₃ | CH₃ | CH₃ | CH₃ | bluish green |

Reacting 2-methyl-3-phenyl-7-dimethylamino-benzopyrylium tetrachloroferrate with p-dibenzylaminosalicylaldehyde by the method described in Example 1 gives the compound 3'-phenyl-7-dibenzylamino-7'-dimethylamino-2,2'-spirodi-(2H-1-benzopyran) of the formula

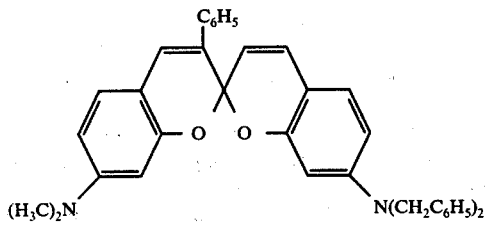

having a melting point of 189° – 191° C.

With electron acceptors, the compound gives a green coloration.

EXAMPLE 6

Hydrogen chloride gas is passed into a solution of 10 parts of methyl isobutyl ketone, 33 parts of p-dimethylaminosalicylaldehyde and 14 parts of zinc chloride in 80 parts of methanol at from 40° to 50° until saturation is reached. The mixture is then stirred for 12 hours at 20° C, the dye is isolated and the cyclizing (decolorizing) is carried out as described in Example 1. The compound 3-i-propyl-7,7'-bis-dimethylamino-spirodi-(2H-1-benzopyran) of the formula

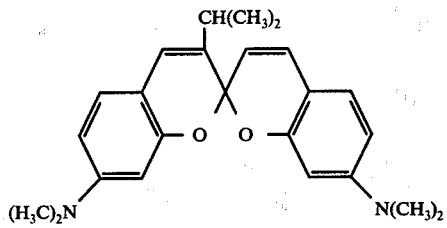

having a melting point of 110° – 112° C, is obtained.

In contact with acidic substances, the compound develops a bluish-green coloration.

The compounds shown below are prepared by the methods described in the preceding examples. The hues developed on contact with acidic substances are shown in the right-hand column.

EXAMPLE 26

19.6 parts of cyclohexanone, 66 parts of p-dimethylaminosalicylaldehyde and 27 parts of zinc chloride are dissolved in 250 parts of methanol. Hydrogen chloride gas is passed in at 40° C until saturation is reached and the mixture is then stirred for 12 hours at 20° C. The dye is isolated and is reacted further by the method described in Example 1. 42 parts of 3,3'-trimethylene-7,7'-bis-dimethylamino-2,2'-spirodi-(2H-1-benzopyran) of the formula

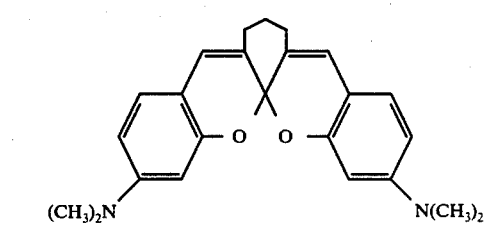

having a melting point of 228° – 230° C are obtained.

In contact with acidic substances, a bluish green coloration is obtained.

EXAMPLE 27

Condensing 4-nonylcyclohexanone with p-dimethylaminosalicylaldehyde by the method described in Example 26 gives 3,3'-(β-nonyltrimethylene)-7,7'-bis-dimethylamino-2,2'-spirodi-(2H-1-benzopyran) of the formula

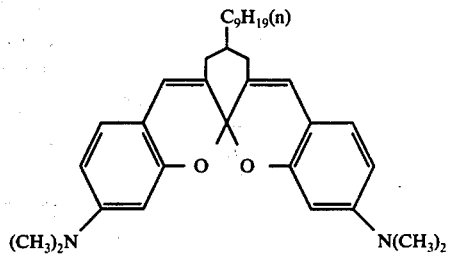

having a melting point of 148° – 150° C.

In contact with acidic substances, the compound develops a bluish green coloration.

EXAMPLE 28

93 parts of 4-tert.-butylcyclohexanone and 232 parts of p-diethylaminosalicylaldehyde are dissolved in 750 parts of methanol. Hydrogen chloride gas is passed into the solution at 40° until saturation is reached and the mixture is then stirred for 12 hours at 20° C. The dye solution is introduced into a mixture of 1,000 parts of toluene and 1,000 parts of 25 percent strength ammonia solution and stirred until completely decolorized. The toluene phase is separated off and concentrated to one-fifth and the oily residue is caused to crystallize by boiling in alcohol. 150 parts of 3,3-(β-tert.-butyltrimethylene)-7,7'-bis-di-ethylamino-2,2'-spirodi-(2H-1-benzopyran) of the formula

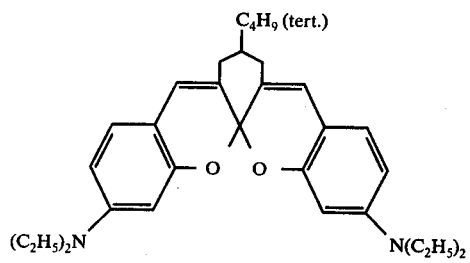

having a melting point of 183° – 184° C are obtained.

In contact with acidic substances, a bluish green coloration is obtained.

EXAMPLE 29

Reacting 4-tert.-butyl-cyclohexanone with p-dibenzylaminosalicylaldehyde by the method described in Example 28 gives 3,3'-(β-tert.-butyltrimethylene)-7,7'-bis-dibenzylamino-2,2'-spirodi-(2H-1-benzopyran) of the formula

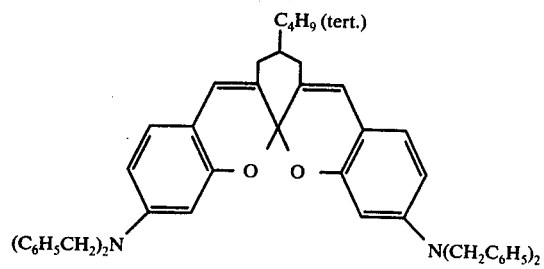

The melting point of the compound is 113° – 116° C.
With acidic substances, the compound develops a bluish green coloration.

EXAMPLE 30

Reacting 4-tert.-butylcyclohexanone with p-dimethylaminosalicylaldehyde by the method described in Example 28 gives the dye intermediate 3,3'-(β-tert.-butyl-trimethylene)-7,7'-bis-dimethylamino-2,2'-spirodi-(2H-1-benzopyran) of the formula

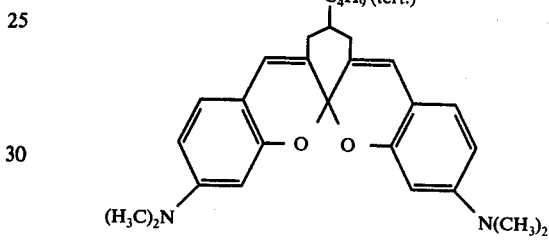

which has a melting point of 247° – 249° C and gives a bluish green color reaction on papers carrying an acidic coating.

The compounds listed in the table which follows were prepared by the methods described in Examples 26 to 30; the hues developed on contact with acidic substances are shown in the right-hand column.

| Example | $R^1$ | $R^2$ | $R^3$ | $R^4$ | $R^5$ | $R^6$ | Hue |
| --- | --- | --- | --- | --- | --- | --- | --- |
| 31 | —CH$_2$—CH(C$_8$H$_{17}$(n))—CH$_2$— | | CH$_3$ | CH$_3$ | CH$_3$ | CH$_3$ | bluish green |
| 32 | —CH$_2$—CH(C$_{12}$H$_{25}$)—CH$_2$— | | CH$_3$ | CH$_3$ | CH$_3$ | CH$_3$ | bluish green |
| 33 | —(CH$_2$)$_3$— | | C$_2$H$_5$ | C$_2$H$_5$ | C$_2$H$_5$ | C$_2$H$_5$ | bluish green |
| 34 | —CH$_2$—CH(C$_4$H$_9$(tert.))—CH$_2$— | | CH$_3$ | p-ClC$_6$H$_4$ | CH$_3$ | p-ClC$_6$H$_4$ | bluish green |
| 35 | —(CH$_2$)$_2$— | | C$_2$H$_5$ | C$_2$H$_5$ | C$_2$H$_5$ | C$_2$H$_5$ | bluish green |
| 36 | —(CH$_2$)$_4$— | | CH$_3$ | CH$_3$ | CH$_3$ | CH$_3$ | bluish green |
| 37 | —CH$_2$—CH(C$_4$H$_9$(tert.))—CH$_2$— | | —(CH$_2$)$_5$— | | —(CH$_2$)$_5$— | | bluish green |
| 38 | —CH$_2$—CH(C$_4$H$_9$(tert.))—CH$_2$— | | C$_2$H$_4$C$_6$H$_5$ | C$_2$H$_4$C$_6$H$_5$ | C$_2$H$_4$C$_6$H$_5$ | C$_2$H$_4$C$_6$H$_5$ | bluish green |
| 39 | —(CH$_2$)$_3$— | | C$_2$H$_4$CN | C$_2$H$_4$CN | C$_2$H$_4$CN | C$_2$H$_4$CN | bluish green |
| 40 | —(CH$_2$)$_3$— | | C$_2$H$_4$Cl | C$_2$H$_4$Cl | C$_2$H$_4$Cl | C$_2$H$_4$Cl | bluish green |
| 41 | —(CH$_2$)$_3$— | | CH$_3$ | C$_2$H$_4$CN | CH$_3$ | C$_2$H$_4$CN | bluish green |
| 42 | —CH$_2$—CH(C$_4$H$_9$(tert.))—CH$_2$— | | H | cyclohexyl | H | cyclohexyl | bluish green |
| 43 | —CH$_2$—CH(C$_4$H$_9$(tert.))—CH$_2$— | | CH$_3$ | C$_2$H$_4$OCH$_3$ | CH$_3$ | C$_2$H$_4$OCH$_3$ | bluish green |

-continued

| Example | R¹ | R² | R³ | R⁴ | R⁵ | R⁶ | Hue |
|---|---|---|---|---|---|---|---|
| 44 | —CH₂—CH—CH₂— with C₇H₁₅(n) | | CH₃ | CH₃ | CH₃ | CH₃ | bluish green |

The following compounds, which were prepared by the methods described in Examples 26 to 30, also give bluish green colorations in contact with acidic substances:

EXAMPLE 45

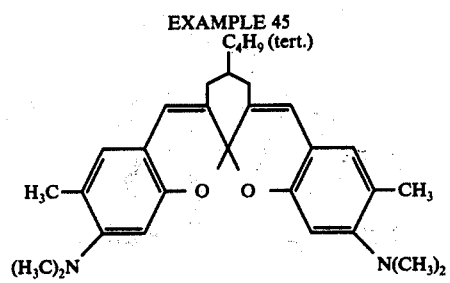

EXAMPLE 46

EXAMPLE 47

EXAMPLE 48

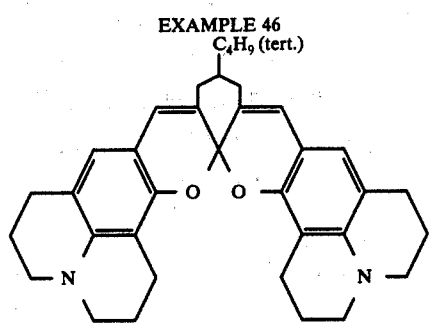

EXAMPLE 49

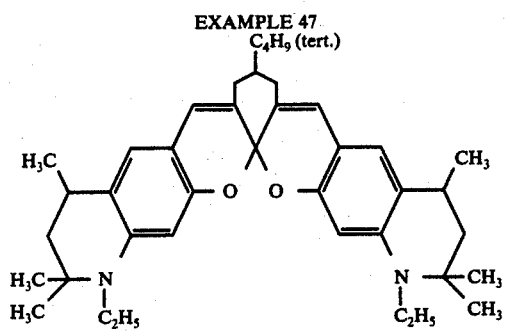

We claim:
1. A dye intermediate of the formula where R¹ is hydrogen, alkyl of 1 to 12 carbon atoms, phenyl which is unsubstituted or substituted by alkyl of 1 to 4 carbon atoms, methoxy, ethoxy, chlorine or bromine, or phenylalkyl of 7 to 10 carbon atoms, R² is hydrogen or R¹ and R² together are dimethylene, trimethylene or tetramethylene, which are unsubstituted or substituted by alkyl of 1 to 12 carbon atoms, R³ and R⁵ each are hydrogen, alkyl of 1 to 12 carbon atoms, cyano-, chlorine-, methoxy- or ethoxy-substituted alkyl of 2 to 4 carbon atoms, cycloalkyl of 5 to 7 carbon atoms, phenylalkyl of 7 to 10 carbon atoms, R⁴ and R⁶ each are alkyl of 1 to 12 carbon atoms, cyano-, chlorine-, methoxy- or ethoxy-substituted alkyl of 2 to 4 carbon atoms, phenylalkyl of 7 to 10 carbon atoms, phenyl which is unsubstituted or substituted by alkyl of 1 to 4 carbon atoms, chlorine or bromine, and the substituents $R^3$, $R^4$, $R^5$ and $R^6$ may be identical or different and the rings A and A' are unsubstituted or substituted by alkyl of 1 to 3 carbon atoms.

2. A dye intermediate of the formula given in claim 1, wherein $R^1$ is phenyl and $R^2$ is hydrogen or $R^1$ together with $R^2$ is β-alkyltrimethylene (where alkyl is of 1 to 12 carbon atoms) and $R^3$, $R^4$, $R^5$ and $R^6$ have the meanings given in claim 1.

3. A dye intermediate of the formula given in claim 1, wherein $R^1$ is phenyl and $R^2$ is hydrogen or $R^1$ and $R^2$ together are β-alkyltrimethylene (where alkyl is of 4 to 12 carbon atoms) and $R^3$, $R^4$, $R^5$ and $R^6$ may be identical or different and each is alkyl of 1 to 6 carbon atoms or benzyl.

4. A dye intermediate as claimed in claim 1, wherein $R^3$, $R^4$, $R^5$ and $R^6$ may be identical or different and each is methyl, ethyl, butyl, propyl, hexyl or benzyl.

5. A dye intermediate as claimed in claim 1, wherein $R^1$ is phenyl and $R^2$ is hydrogen or $R^1$ and $R^2$ together are β-alkyltrimethylene (where alkyl is of 4 to 12 carbon atoms) and $R^3$, $R^4$, $R^5$ and $R^6$ may be identical or different and each is methyl, ethyl, butyl, propyl, hexyl or benzyl.

6. A dye intermediate of the formula given in claim 1, wherein $R^1$ is phenyl and $R^2$ is hydrogen or $R^1$ and $R^2$ together are β-tert.-butyl-trimethylene and $R^3$, $R^4$, $R^5$ and $R^6$ may be identical or different and each is methyl, ethyl, propyl, butyl, hexyl or benzyl.

7. A dye intermediate of the formula

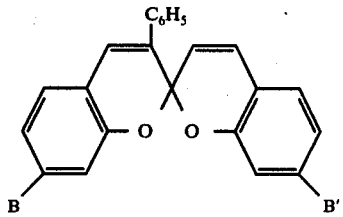

where B and B' are $-N(CH_3)_2$, $-N(C_2H_5)_2$ or

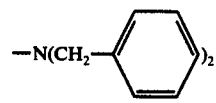

or B is $-N(CH_3)_2$ and B' is

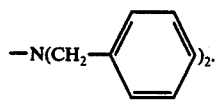

8. A dye intermediate of the formula

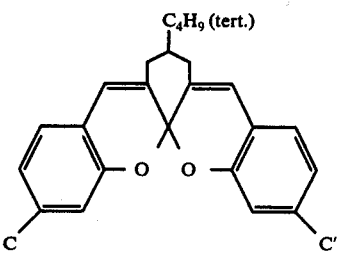

where C and C' are $-N(C_2H_5)_2$ or

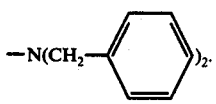

* * * * *